United States Patent
Freestone et al.

(10) Patent No.: US 9,796,958 B2
(45) Date of Patent: Oct. 24, 2017

(54) BACTERIAL GROWTH ENHANCER

(75) Inventors: Primrose Pamela Elaine Freestone, Wigston (GB); Richard David Haigh, Leicester (GB); Mark Lyte, Wolfforth, TX (US)

(73) Assignee: Plant Bioscience Limited, Norwich (GB)

( * ) Notice: Subject to any disclaimer, the term of this patent is extended or adjusted under 35 U.S.C. 154(b) by 1359 days.

(21) Appl. No.: 12/092,956

(22) PCT Filed: Nov. 7, 2006

(86) PCT No.: PCT/GB2006/050371
§ 371 (c)(1),
(2), (4) Date: Nov. 5, 2008

(87) PCT Pub. No.: WO2007/052081
PCT Pub. Date: May 10, 2007

(65) Prior Publication Data
US 2009/0087517 A1   Apr. 2, 2009

(30) Foreign Application Priority Data

Nov. 7, 2005 (GB) .................................. 0522593.3

(51) Int. Cl.
C12N 1/38 (2006.01)
A23L 1/212 (2006.01)
C12Q 1/04 (2006.01)
A23C 9/133 (2006.01)
A23L 19/00 (2016.01)

(52) U.S. Cl.
CPC .............. *C12N 1/38* (2013.01); *A23C 9/133* (2013.01); *A23L 19/09* (2016.08)

(58) Field of Classification Search
USPC .................. 426/34, 61; 435/29, 252.1, 252.9
See application file for complete search history.

(56) References Cited

U.S. PATENT DOCUMENTS 4,267,196 A  *  5/1981  Johnston .......................... 426/49
5,571,441 A     11/1996  Andon et al.
5,629,349 A      5/1997  Lyte

OTHER PUBLICATIONS

Chan-Blanco et al. "Using banana to generate lactic acid through batch process fermentation." Applied Microbiology and Biotechnology. vol. 63, No. 2, Dec. 2003. p. 147-152.*
Nikibone.com. "Banana Recipes." Archived Jan. 2003.*
Herich et al. "Lactic acid bacteria, probiotics and imun system." Vet Med. Czech, 47.R 2002.*
Fermentation Technology. "Viscosity of Fermentation Broth and the Choice of the Right Impeller." Jan. 2012.*
Ritter et al. "Evaluation of the passage of *Lactobacillus gasseri* K7 and bifobacteria from the stomach to intestines using a single reactor model". May 8, 2009.*
Everyday Food. "Banana-Blueberry Smoothie". Mar. 2005.*

(Continued)

*Primary Examiner* — Nikki H Dees
*Assistant Examiner* — Amber Cox
(74) *Attorney, Agent, or Firm* — Lando & Anastasi, LLP

(57) ABSTRACT

We describe the production and use of an extract obtained from *Musa* spp., preferably from bananas, in the promotion of growth of Gram-positive bacteria such as lactic acid bacteria. The extract is also useful for growth enhancement of environmentally-stressed Gram negative bacteria. Fermented foods containing such extracts are also described.

18 Claims, 6 Drawing Sheets

(56) References Cited

OTHER PUBLICATIONS

Tsen et al. "Fermentation of banana media by using k-carrageenan immobilized *Lactobacillus acidophilus*," International Journal of Food Microbiology 91 (2004) 215-220.*

Tsen et al. "Banana puree fermentation by *Lactobacillus acidophilus* immobilized in Ca—alginate." J. Gen. Appl. Microbial., 49, 357-361 (2003).*

(Moro) Hansen, "BCRC 10695" http://www.straininfo.net/strains/505800/browser pp. 1-2.*

Scott, W. E., McKay, H. H., Schaffer, P. S., & Fontaine, T. D. (1949). The Partial Purification and Properties of Antibiotic Substances From the Banana (Musa Sapientum) . Journal of Clinical Investigation, 28(5 Pt 1), 899-902.*

Aegerter, P. et al., "Culture of 5 Commonly Used Acid Producing Bacteria on Banana Pulp", Applied and Environmental Microbiology, vol. 39, No. 5, 1980, pp. 937-942.

Lyte, Mark. "Induction of Gram-Negative Bacterial Growth by Neurochemical Containing Banana (Musa X Paradisiaca) Extracts", FEMS Microbiology Letters, vol. 154, No. 2, 1997, pp. 245-250.

International Search Report for PCT/GB2006/050371 mailed Apr. 19, 2007.

Karsheva et al. "Rheological Behavior of Fermentation Broths in Antibiotic Industry". Applied Biochemistry and Biotechnology, vol. 68: 187-206. (1997).

Kleerebezem et al. "Probiotic and Gut *Lactobacilli* and *Bifidobacteria*: Molecular Approaches to Study Diversity and Activity". Annu. Rev. Microbiol. 2009. 63: 269-290.

Chen et al. "Isolation and Characteristics of Lactic Acid Bacteria Isolated from Ripe Mulberries in Taiwan". Brazilian Journal of Microbiology. vol. 41, pp. 916-921. 2010.

Cronin et al. "Development of a Luciferase-based Reporter System to Monitor *Bifidobacterium* breve UCC2003 Persistence in Mice". BMC Microbiology. vol. 8, No. 161. 2008.

Orhan, Ilkay. "Biological Activities of Musa Species". J. Fac. Pharm. Ankara, vol. 30, pp. 39-50. 2001.

* cited by examiner

BACTERIAL GROWTH ENHANCER

The application is a US national phase application under 35 U.S.C. §371 of PCT/GB2006/050371, filed on Nov. 7, 2006, which claims priority to GB Serial Number 0522593.3, filed Nov. 7, 2005, all of which are incorporated herein by reference, in its entirety.

FIELD OF THE INVENTION

The present invention relates to methods and compositions for enhancing or promoting growth of bacteria, and in particular lactic acid bacteria. Aspects of the invention relate to foodstuffs and dietary supplements containing such compositions. Certain aspects of the invention relate to methods for detecting bacterial contamination in cultures.

BACKGROUND TO THE INVENTION

Lactic acid bacteria (LAB) are Gram-positive commensals of the mammalian gastrointestinal tract that have also been used in food preservation for millennia. In more recent industrialised eras, co-incident with the development of Microbiology as a scientific discipline, they have been used more systematically, and now form the foundation of worldwide dairy and food fermentation industries (cheese, yoghurts, fermented hams and sausages, condiments such as fish and soy sauces). In the last few decades LAB have been ingested directly for human and animal health purposes in the form of probiotic yoghurts, beverages and other supplements. Although environmentally ubiquitous, LAB are nutritionally fastidious bacteria, whose culture is complex, involving specialised microaerophilic atmospheres and specific, multi-component culture media. Thus any new innovation which can simplify either cultivation parameter without requiring significant changes in existing fermenter technology is likely to find wide scale application.

Although very important in the dairy, fermented food and more recently health care associated industries, LAB are regarded as unwelcome contaminants in the brewing and wine production industries. Lactic acid bacteria possess a remarkable ability to survive in liquid media that are acidic, cold and anaerobic. These are the typical physical characteristics of beer, lagers and wine, and are environmental conditions that most other microbes find very hostile. In addition to their tolerance of such conditions, lactic acid bacteria also have the tendency to ferment any residual sugars they encounter in beer or wine to lactic acid, which, along with other LAB metabolites, can impart undesirable sour and similar 'off' tastes. Thus, there is a considerable global market in media for LAB diagnostics in the beverage fermentation industries. LAB isolates from beer and wine are generally difficult to culture, as they have undergone considerable environmental stresses during the various fermentation procedures they will have experienced and are often slow to revert to active growth. It can take up to a week to culture beer LAB contaminants on the optimal culture media for LAB, MRS medium, and indeed some LAB contaminants can take even longer than this to be restored, which can have disastrous consequences for the fate of the contaminated beverage during its subsequent long storage/maturation process.

The identification of factors which can enhance or promote growth of LAB is therefore of considerable commercial significance.

Bananas (*Musa* spp) are known to have a number of properties which can affect the growth of bacteria. It has been reported (Lyte, 1997, FEMS Microbiology Letters 154:245-250) that extract from bananas can promote the growth of Gram negative bacteria such as *E. coli*. The effects of the banana extract growth induction were found to be due to the presence of neurochemicals such as noradrenaline (norepinephrine) and dopamine in the banana extract.

U.S. Pat. No. 5,629,349 describes the initial use of neurochemicals in growth enhancement of bacteria, and cites references foodstuffs such as bananas and plantains as sources of dietary noradrenaline and dopamine. However, the 1997 Lyte publication stated that no effect of either the banana extract or neurochemical supplements could be seen on the growth of Gram positive bacteria.

International Patent Application WO2004/069143 describes the medicinal use of banana or plantain extract for treatment of inflammatory bowel disease; the publication suggests that banana extract will prevent or inhibit bacterial growth, and may prevent bacterial adhesion to the intestinal wall.

The present inventors have surprisingly found that, contrary to the reported suppressive effects on Gram positive bacterial growth of bananas, a banana extract can actually promote growth of Gram positive bacteria, and of LAB in particular. We have also determined that the extract effectively promotes growth of environmentally stressed bacteria. We further believe that the extract may be used to improve the viability of a bacterial sample.

It is also believed that extracts having the same or similar properties may be obtained from other plants; in particular apple, orange, plum, carrot, tea, and coffee.

SUMMARY OF THE INVENTION

According to a first aspect of the present invention, there is provided a method of promoting growth of Gram positive bacteria, the method comprising providing bacteria with an extract obtainable from *Musa* spp.

By "promoting growth", we mean that growth of the bacteria is enhanced over growth which would be obtained in the absence of the extract. In certain embodiments of the invention, growth of bacteria is enhanced over growth which would normally be expected from a medium typically used to grow that type of bacteria. For example, MRS Agar is typically used for growth of lactic acid bacteria (LAB); as described herein, LAB growth is enhanced on MRS Agar incorporating *Musa* extract.

Preferably the extract is obtained from *Musa* spp, and more preferably from bananas. We believe that many or most commercial varieties of banana may be used; other banana varieties or plantains may also provide useful extract. The banana used is preferably *Musa×paradisiaca*. The extract is preferably obtainable from or obtained from whole skin, whole pulp, or both skill and pulp of the fruit. The active components of the extract have yet to be determined, but preferably the extract does not substantially comprise catecholamines, and/or fructo-oligosaccharides. It is believed that the active principle of the extract is not a catecholamine, based on the reports of Lyte (1997), who exclusively used a serum-supplemented medium to demonstrate banana and catecholamine growth enhancement. The observations reported herein indicate that banana extract is able to enhance growth in non-serum based culture media, while Freestone et al (2000) (Journal of Bacteriology 182: 6091-6098) showed that catecholamines such as noradrenaline did not enhance growth in non-serum containing culture media. Collectively, this indicates that the components in banana responsible for the growth observed are not catecholamines.

Preferably the bacteria are lactic acid bacteria, conveniently selected from lactobacilli and bifidobacteria. Particularly preferred species include *Lactobacillus* sp. The bacteria may be environmentally stressed prior to growth with the extract.

The method may comprise the step of growing the bacteria in a non-anaerobic environment; conveniently in standard atmosphere. It has been surprisingly identified that the extract of the present invention permits anaerobic bacteria such as LAB to be grown in air, rather than in specialised anaerobic conditions.

The invention also provides a method of promoting growth of environmentally stressed Gram negative bacteria, the method comprising providing bacteria with an extract obtainable from *Musa* spp. In addition to promoting growth of Gram positive bacteria, the inventors have found that the extract of the invention will promote recovery and growth of stressed Gram negative bacteria. The bacteria conveniently comprise pathogenic and/or enteric bacteria, such as *E. coli, Listeria* sp, and the like.

The invention further provides a method of improving viability of bacteria in a sample, the method comprising providing bacteria with an extract obtainable from *Musa* spp. Preferably the bacteria are Gram positive bacteria, more preferably lactic acid bacteria, and most preferably *Lactobacillus* sp. The sample may be a foodstuff, conveniently a fermented foodstuff, for example yoghurt.

A further aspect of the invention provides a method of promoting adherence of bacteria to a substrate, and/or of increasing viscosity of a bacterial sample, the method comprising providing bacteria with an extract obtainable from *Musa* spp. Preferably the bacteria are Gram positive bacteria, more preferably lactic acid bacteria, and most preferably *Lactobacillus* sp. The sample may be a foodstuff, conveniently a fermented foodstuff, for example yoghurt. The surface may be an artificial substrate, such as a culture dish or culture medium, but in certain embodiments may be a biological substrate; for example the intestinal wall or similar.

According to a further aspect of the present invention, there is provided a bacterial growth medium comprising an extract obtainable from *Musa* spp. The medium may be liquid or solid. Preferably the medium includes minimal additional nutrient components; a preferred medium is based on deMann Rogan Sharpe (MRS) medium or Luria broth, although other basic culture media may be used instead. The medium preferably does not comprise serum. The extract may be present in the medium at a concentration of between 0.01 to 10%, preferably 0.1 to 5%, and more preferably 1 to 2%. The medium is preferably for growth of Gram positive bacteria, and more preferably for lactic acid bacteria. However, the medium will also be suitable for other bacterial species, too.

The invention further provides a bacterial growth supplement comprising an extract obtainable from *Musa* spp. The supplement may be formulated for addition to growth medium. The supplement may be in solid or liquid form, and may be lyophilised extract.

According to a further aspect of the present invention, there is provided a method of detecting the presence of Gram positive bacteria in a sample, the method comprising introducing said sample to a bacterial growth medium comprising an extract obtainable from *Musa* spp, and culturing the sample on the medium. The sample may be taken from a food product, preferably a fermented food product, or may be taken from a brewing or winemaking product. The culturing step may be undertaken in non-anaerobic or anaerobic conditions. The bacteria are preferably lactic acid bacteria. The bacteria may be environmentally stressed.

The invention also provides a method of detecting the presence of environmentally stressed Gram negative bacteria in a sample, the method comprising introducing said sample to a bacterial growth medium comprising an extract obtainable from *Musa* spp, and culturing the sample on the medium.

Also provided is a kit for detecting the presence of Gram positive bacteria, or of environmentally stressed Gram negative bacteria, in a sample, the kit comprising bacterial growth medium including an extract obtainable from *Musa* spp.

The invention also provides a method for producing an extract from *Musa* spp for use in promoting bacterial growth. The method comprises blending at least a portion of a *Musa* fruit in a suitable diluent. The diluent is preferably water. The method may comprise blending a whole fruit, fruit pulp, or fruit skin. The method may also comprise any or all of the following additional steps: filtering and/or centrifuging the blended extract to remove debris; drying or lyophilising the extract; freezing the extract, preferably at no less than −20° C.; and sterilising the extract, for example by filter sterilisation, pasteurisation, or autoclaving. The invention also extends to extract produced according to such a method.

A yet further aspect of the invention provides a method of preparing a fermented food, the method comprising adding an extract obtainable from *Musa* spp to said food, or to an unfermented or partially fermented precursor to said food. The food is preferably fermented by the action of Gram positive bacteria, and more preferably lactic acid bacteria. The food may comprise a dairy food, for example, cheese, yoghurt, and the like, or may comprise a meat product.

Also provided is a fermented food comprising an extract obtainable from *Musa* spp. The invention also provides a fermented food comprising a bacterial growth enhancer, wherein the growth enhancer is an extract obtainable from *Musa* spp. The food preferably also comprises Gram positive bacteria, and more preferably lactic acid bacteria.

The invention still further provides a nutritional supplement comprising an extract obtainable from *Musa* spp. The supplement may also comprise bacteria, preferably Gram positive bacteria, and more preferably lactic acid bacteria. The invention also provides a probiotic supplement comprising an extract obtainable from *Musa* spp. The supplement may also comprise bacteria.

The present invention also provides the use of an extract obtainable from *Musa* spp in the preparation of a supplement for promoting growth of bacteria, preferably Gram positive bacteria, and more preferably lactic acid bacteria. The supplement may be in the form of a foodstuff or a nutritional supplement for human or animal consumption, or may be a supplement for addition to bacterial growth media or the like.

In addition to *Musa* spp, we believe that the active component or components of the extract may be found in other plant species. The extract is preferably obtained from the fruit of the plant, but may be obtained from the leaves (for example, where the plant is tea) or roots (for example, where the plant is carrot). Accordingly, the present invention also provides a method of promoting growth of lactic acid bacteria, the method comprising providing lactic acid bacteria with an extract obtainable from or obtained from a plant selected from the group comprising apple, orange, plum, carrot, tea, and coffee. The invention also provides a bacterial growth medium comprising an extract obtainable from or obtained from a plant selected from the group comprising apple, orange, plum, carrot, tea, and coffee; and a method of detecting the presence of lactic acid bacteria in a sample, the method comprising introducing said sample to a bacterial growth medium comprising an extract obtainable or obtained from a plant selected from the group comprising apple, orange, plum, carrot, tea, and coffee, and culturing the sample in or on the medium.

Further aspects of the invention provide a method of preparing a fermented food, the method comprising adding an extract obtainable or obtained from a plant selected from the group comprising apple, orange, plum, carrot, tea, and coffee to said food, or to an unfermented or partially fermented precursor to said food. The invention further provides a fermented food comprising an extract obtainable or obtained from a plant selected from the group comprising apple, orange, plum, carrot, tea, and coffee; and a fermented food comprising a bacterial growth enhancer, wherein the growth enhancer is an extract obtainable or obtained from a plant selected from the group comprising apple, orange, plum, carrot, tea, and coffee.

Aspects of the invention also provide a nutritional supplement comprising an extract obtainable or obtained from a plant selected from the group comprising apple, orange, plum, carrot, tea, and coffee; and a probiotic supplement comprising an extract obtainable or obtained from a plant selected from the group comprising apple, orange, plum, carrot, tea, and coffee.

BRIEF DESCRIPTION OF THE FIGURES

These and other aspects of the present invention will now be described by way of example only with reference to the accompanying figures, in which.

DETAILED DESCRIPTION OF THE FIGURES

Production of Banana Extract

Figure 1:
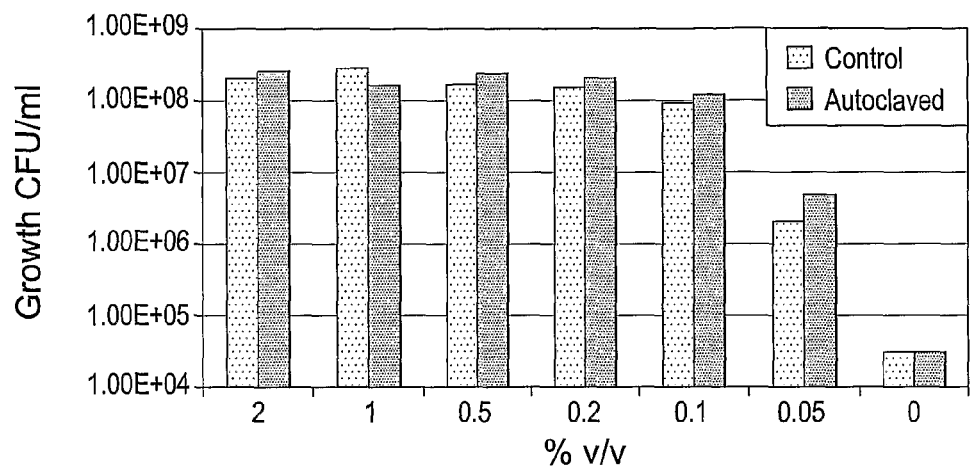
FIG. 1 shows the heat stability of banana extract after autoclaving

We refer herein to the banana extract as 'banana factor' or BF. The extract may be produced from banana pulp, or from banana skin.

Banana Pulp

1. Peeled banana pulp is liquidised with water in a food blender to a smooth paste, at a ratio of 100 ml of distilled water per 250 g of fruit pulp. The liquidised pulp is then centrifuged for 20 minutes at 8000 rpm to remove pips and other debris. The resulting viscous liquid, a crude banana juice, is then decanted. This juice can then be further processed in one of 4 ways:

2. Added directly with no further processing to culture media, which must then be sterilised (see 4. below). At the recommended supplementation of 1-2% v/v, this produces culture media which has a few speckles of fruit tissue, but which does not affect visualisation of colonies. It is also possible to lyophilise to dryness this crude pulp juice, and reduce the dried material (which is a greyish honeycomb like substance) to powder using a coffee grinder. This dried banana powder can also be directly incorporated into dry culture media.

3. With no further processing, the crude pulp can be stored at −20° C. (to prevent microbial contamination and minimise oxidative modifications from endogenous oxidases), until required for use (such as detailed in 2. above).

4. Sterilisation of the crude banana pulp can be achieved by passage of the extract through a 0.2 or 0.45 micrometer filter, though since phenolate oxidases will still be active in such preparations, it is recommended that either this extract be added directly to media, which must then autoclaved, or it is stored at −20° C.

5. Autoclaving can be used to preserve the banana extract, as this will inactivate most degradative enzyme activities, as well as sterilising the pulp extract. The active growth inducing agents in BF are fully stable to autoclaving. However, it will be clear to one skilled in the art that consecutive pasteurisation and filtration steps could also provide a satisfactory, less energy consuming method of combined stabilisation and sterilisation.

6. For preservation by autoclaving, the extract is decanted into heatproof glass bottles and heated for 15 minutes, at 121° C., 15 lbs in$^{-2}$ (103 kPa). After autoclaving, the resulting preparation is aseptically decanted into sterile centrifuge tubes, and centrifuged at 8000 rpm to remove any precipitated material. This extract, now termed BF, is aseptically decanted into fresh, sterile tubes or bottles, which are stable to storage at 4° C. or −20° C.

7. A second batch of BF activity can also be obtained by re-extracting the pip and cellular debris pellet described in 1. above with water, at a ratio of half the volume of banana pulp centrifuged e.g. 500 ml of water to extract banana debris from an original pulp volume of 1000 ml. The extraction procedure involves re-suspending the debris pellet in the water, followed by vigorous mixing for around 5 minutes. This second BF extract is re-centrifuged for 20 minutes at 8000 rpm. Further extractions are possible, though these contain considerably less activity and may therefore not be cost-effective to pursue.

8. Activity recoveries from a typical extraction are shown in Table 1. BF activity levels are measured using a biological growth assay, defined as follows: A "Unit of Activity" of BF activity is defined as follows: A unit of activity (U) is the quantity of BF preparation required to stimulate the growth of test strain E. coli E2346/89 from an initial inoculum of approximately $10^2$ CFU/ml to $10^7$ CFU/ml, under the following culture conditions: 18 hours static growth at 37° C. in a 5% $CO_2$/air humidified incubator in serum-SAPI medium. Serum-SAPI medium is 6.25 mM $NH_4NO_3$, 1.84 mM $KH_2PO_4$, 3.35 mM KCl, 1.01 nM $MgSO_4$ and 2.77 mM glucose (pH 7.5) supplemented with 30% (v/v) adult bovine serum.

9. BF can be used directly, or lyophilised to dryness, and re-constituted with water at volumes of up to 20% of the original volume of extract (i.e. concentrated by a factor of at least 5-fold).

Preparation of Banana Skin Extracts

1. Pulp-free banana skins are chopped into approximately 1 cm pieces, and then blended with water at a ratio of 100 ml of water per 100 g of skin until a smooth but fibrous extract is obtained. This extract is then centrifuged for 20 minutes at 8000 rpm to remove cellulose and other debris. The resulting liquid is then decanted.

2. Although this extract is less viscous than the pulp extract, and can therefore be readily filter sterilised, because of high endogenous oxidase activity in the skin, it is recommended that the extract be incorporated into culture media and autoclaved immediately, or that the skin extract be autoclaved before use.

3. Although banana skin possesses less growth inducing activity than the pulp, a media supplementation of 1-2% v/v of the skin extract is sufficient to induce high level growth stimulation. It is possible to concentrate lyophilised skin extract by a factor of at least 10-fold.

TABLE 1

Typical purification data

| Stage | Total volume | Activity U/ml | Total Activity U | Recovery % |
|---|---|---|---|---|
| Crude pulp juice | | | | |
| Extraction 1 | 800 | 1330 | 1 064 000 | 100 |
| Extraction 2 | 500 | 1000 | 500 000 | 100 |
| After autoclaving | | | | |
| Extraction 1 | 800 | 1400 | 1 120 000 | 100 |
| Extraction 2 | 500 | 950 | 475 000 | 95 |
| After lyophilization and final preparation (diluted to original vol) | Based on re-constitution of 10 ml test volume | Ext. 1 1250 Ext. 2 900 | 1 000 000 450000 | 94 90 |

Stability Analyses
Heat Stability

The banana juice extract is highly stable to heat treatment and can be autoclaved (121° C. for 20 minutes) without significant loss of activity. This is demonstrated in FIG. 1, which shows the growth response of test strain E. coli E2346/89 in serum-SAPI medium to a dilution series of control and autoclaved BF. Growth conditions were as described in section 8 above (18 hrs incubation at 37° C.); the values shown are means of duplicate plate counts.

Preliminary Analysis of the Growth-Enabling Components within BF

1. Comparison of BF with Dietary Phenolates

Figure 2:
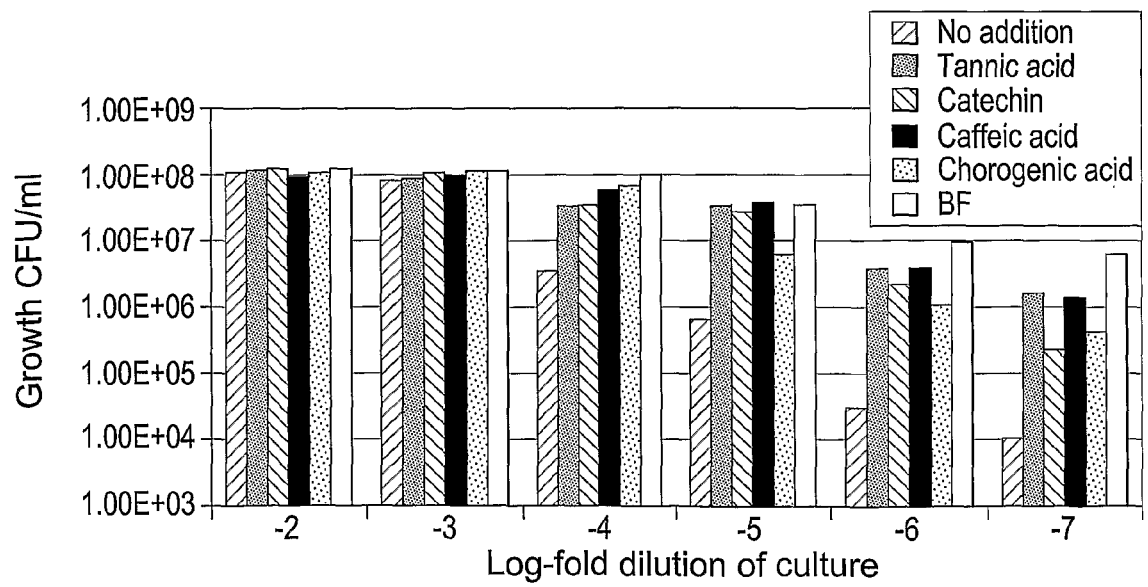
FIG. 2 shows the growth response of L. casei to dietary catecholates compared with banana extract. Tannic acid was used at 50 µg/ml, the other compounds were all used at 100 µM, final concentration; BF was used at 2% v/v. Cultures were grown statically for 24 hrs 37° C. in a humidified incubator; the values shown are representative data from several similar analyses and are means of triplicate plate counts.

BF is prepared from the pulp of the banana fruit, though banana skin also possesses some growth enhancement activity. Banana pulp extracts contain a variety of compounds that have been shown by various researchers of being able to modulate growth of LAB, including sugars, minerals and various dietary phenolates. Shown in FIG. 2 is the growth response of L. casei to certain of these phenolates, compared with growth response to the BF preparation. All the phenolate compounds shown are suitable for human consumption, though highly expensive when used in purified form and individually are less effective than the much more economical BF. Note that the growth analyses shown below were in vitro assays performed in serum-based SAPI, a minimal salts microbiological culture medium which provides an intentionally stressful culture environment containing immunological and nutrient challenges reflective of those which will be experienced in vivo. In this medium the LAB grow normally poorly when inoculated with low cell numbers. However substantial log-fold improvements in growth were obtained when cultures were supplemented with BF, as well as the individual phenolates present in BF, suggesting that BF is likely to be functional in LAB growth enhancement in vivo if co-consumed with probiotic LAB species. However, while BF is able to enhance growth in non-serum-based media, the dietary phenolates shown in FIG. 2 are not (Freestone, data not shown). This suggests that while the individual dietary phenolates may increase growth in serum-supplemented medium, their contribution to the enhancement of LAB or other species growth in laboratory culture media such as MRS or Luria broth is functionally less important.

2. Analyses of the Mechanism by which BF and Dietary Phenolates Induce Lab Growth A paper (Lyte, 1997) was published in 1997 detailing the ability of banana pulp extracts (created by blending and filter-sterilisation only) to induce growth of pathogenic enteric bacteria. The author, Mark Lyte found that banana skin and pulp extracts had no effects on Gram-positive bacteria (LAB are classified as being Gram-positive). The conclusion from the results of several experiments was that the active components in banana pulp and skin were the catecholamines noradrenaline and dopamine. All of these analyses performed in this publication were done in serum-based media. While LAB do show around 2 log-fold increases in response to noradrenaline and dopamine, this growth enhancement only occurs in serum-based media (our unpublished data). Previous work has shown that the catecholamines noradrenaline and dopamine induce growth in iron-restricted media such as serum via provision of Fe from host iron-sequestering proteins such as transferrin or lactoferrin (Freestone et al 2000, Journal of Bacteriology 182: 6091-6098; Freestone et al 2002 Shock 18:465-470; and Freestone et al 2003 FEMS Microbiol. Lett. 222: 39-43) (note that the main bacteriostatic factor in serum is transferrin, and in mucosal secretions lactoferrin). While the catecholamines and other phenolate compound present within banana extracts can deliver iron from host iron binding proteins to Gram-negative species such as E. coli (Table 2) it is clear that the same compounds are not acting in a similar manner, that is deliverance of Fe, with respect to the Gram-positive L. casei. Further evidence for a different method of growth induction by banana-derived compounds comes from our demonstration of the utility of autoclaved BF to enhance bacterial growth in standard non-serum-containing LAB-specific and other microbial culture media (see FIGS. 3-7). It is clear therefore, that the mechanism of growth stimulation by BF, specifically the dietary phenolates and catecholamines contained within BF, is different in Gram-positive LAB species from that demonstrated in Gram-negative bacteria such as E. coli.

TABLE 2

Ability of BF and dietary catecholamines and catecholates to mediate delivery of lactoferrin-complexed Fe to *L. casei* and *E. coli*

| Addition | $^{55}$Fe incorporation/ml of culture *L. casei* | $^{55}$Fe incorporation/ml of culture *E. coli* |
| --- | --- | --- |
| None | 66 | 376 |
| Noradrenaline | 29 | 8542 |
| Dopamine | 48 | 6815 |
| Caffeic acid | 29 | 11385 |
| Catechin | 57 | 3931 |
| Chlorogenic acid | 28 | 7374 |
| Tannic acid | 28 | 13952 |
| Banana (BF) | 409 | 14220 |

*L. casei* and *E. coli* were added at around $5\times10^6$ CFU/ml to triplicate 1 ml serum-SAPI medium containing the additions shown in Table 2, and $2\times10^5$ cpm/ml of $^{55}$Fe-complexed human lactoferrin. Tannic acid was used at 50 μg/ml, the other compounds were all used at 100 μM, final concentration; BF was used at 2% v/v. Cultures were incubated as described in the legend to FIG. 2, and growth enumerated on MRS agar (*L. casei*) or Luria agar (*E. coli*). $^{55}$Fe incorporation was determined by scintillation counting of triplicate washed bacteria cultures.

All of the cultures were similar in terms of final cell numbers, although when centrifuged and washed the banana (BF)-supplemented LAB culture giving the higher $^{55}$Fe incorporation count was found to have produced large amounts of exopolysaccharide and were very viscous, possibly explaining the higher incorporation of $^{55}$Fe (due to trapping of $^{55}$Fe-lactoferrin within the sticky exopolysaccharide produced by the LAB under this particular set of growth conditions).

Agar Plate Assays

FIGS. 3 to 6 show photographs of agar plates with and without banana extract used to grow test strains of *Lactobacillus casei* under various conditions and at various dilutions. The photographs show the growth promoting properties of banana extract.

Figure 3:
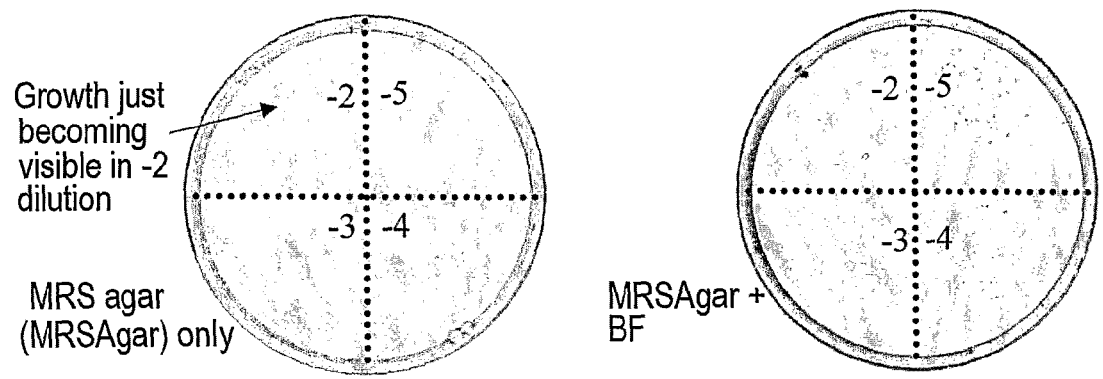
FIG. 3 shows growth of L. casei on agar plates with and without banana extract

FIG. 3 shows agar plates made with MRS medium (left photograph) with the addition of BF (right photograph). MRS medium (a very widely used LAB-specific culture medium) was solidified with 1.5% bacteriological agar (hereafter referred to as MRSAgar). The LAB used were taken directly from a Danacol brand *L. casei* probiotic supplement suspension and serially diluted in MRS liquid medium, in steps of 1:100 [−2 dilution], 1:1000 [−3], 1:10,000 [−4] and 1:100,000 [−5]. 50 μl of each dilution was then pipetted onto the MRSAgar plates, which were then incubated for 36 hours at 37° C. in a humidified $CO_2$ incubator.

Even though MRS medium is the preferred media for culture of the nutritionally fastidious LAB, it is typical for healthy non-environmentally stressed LAB to take 3 days or more to shown visible growth of individual colonies. In contrast, supplementing MRSAgar with BF enables growth to visible levels of all dilutions at this time point.

The ability of LAB to subsist within acidic, anaerobic environments hostile to most microbial species, plus their fermentation of available sugars to lactic acid, makes them undesirable souring agents in the brewing and wine making industries (LAB also cause sliminess in certain vinegar generators). Currently, quality control (QC) analysis of beer and wine involves plating test samples on MRSAgar, for between 3 and 7 days (control LAB strains can take up to 3 days to grow on MRSAgar; environmental isolates can take up to 7 days or even longer). The economic advantages in reducing the time to detection to around 1 day are obvious.

Figure 4:
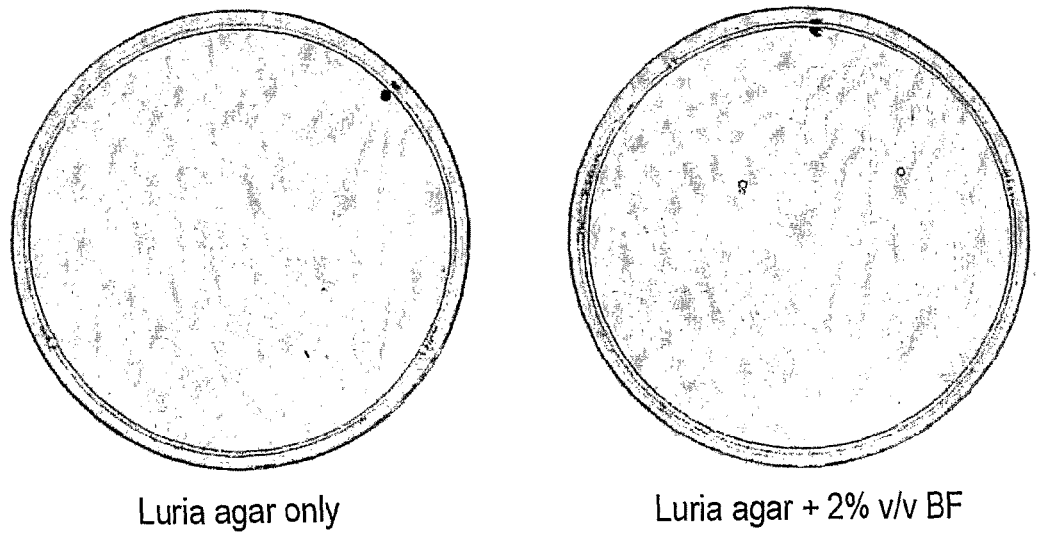
FIG. 4 shows bacterial growth after 16 hours of 50 µl of L. casei ($10^8$ CFU/ml suspension) streaked out onto Luria agar with (right hand picture) and without (left hand picture) banana extract at 2% v/v.

FIG. 4 shows plates with Luria agar only (left image) and Luria agar plus BF (right image). Luria agar (LA) is a general laboratory medium for less nutritionally fastidious bacteria such as *E. coli* and *Salmonella*. Though LA is considerably cheaper than MRSAgar it is not normally used for culture of LAB because the LAB will grow very slowly on it, taking at least 5 days to grow to visible colony size. However, when the LA was supplemented with 2% v/v BF extract, strong, visible growth of LAB was seen after a single overnight incubation at 37° C. The significance of this experiment is that LAB, such as *L. casei*, can now be grown on less complex (and substantially cheaper) media with BF extract supplementation. Furthermore, this result begs the question of just how simple the media composition for growing LAB could become when supplemented with BF extracts.

Figure 5:
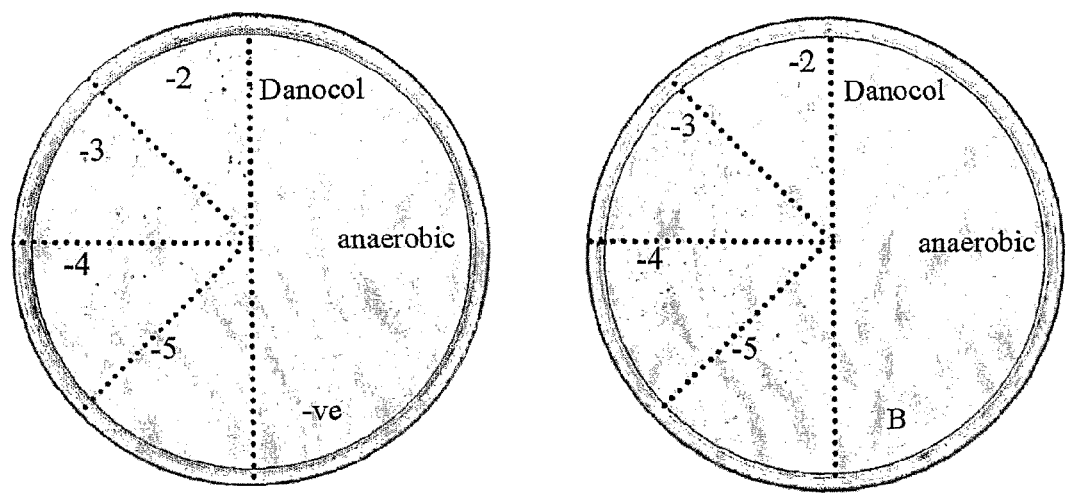
FIG. 5 shows bacterial growth under anaerobic conditions with banana extract

FIG. 5 demonstrates the growth of bacteria on MRSAgar without BF (left image) and with BF (right image) under anaerobic conditions. In this experiment (MRSAgar only [−ve on the image] or MRSAgar with 2% BF [B on the image]) there can be seen the growth levels of serially-diluted *L. casei* (from a probiotic beverage brand name Danacol, manufacturer Danone) after 36 hours under anaerobic conditions at 30° C. While it is clear that there is growth on the MRSAgar only plates, there is also substantially more on the BF-supplemented medium. This result combined with the data from FIGS. 3, 4, 6 and 7 indicates that BF is likely to be functional in most aerobic and anaerobic LAB culture protocols.

Figure 6:
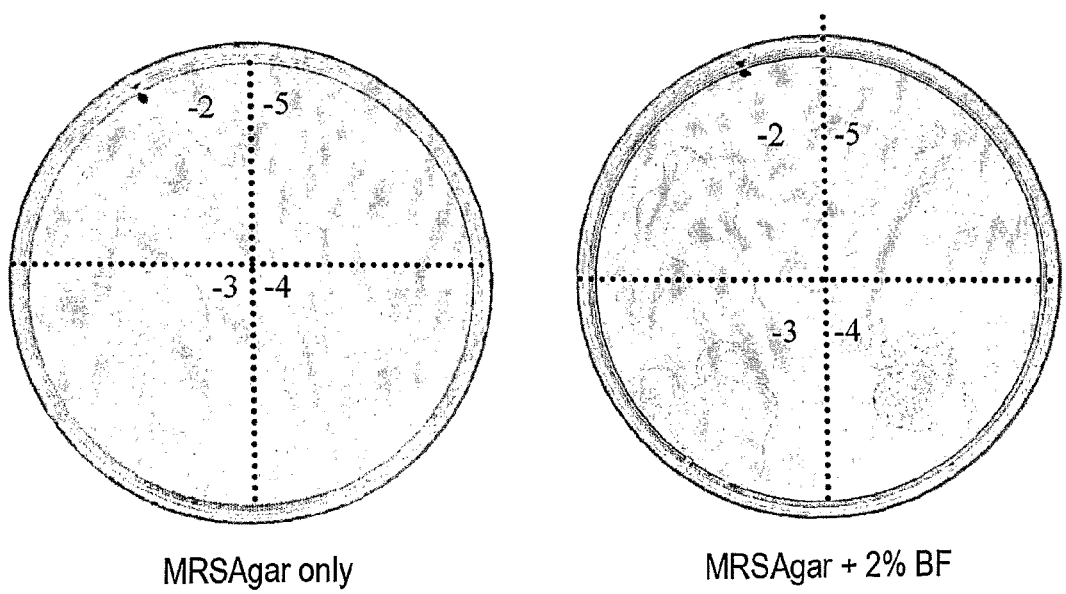
FIG. 6 shows growth of environmentally stressed E. coli with banana extract

FIG. 6 demonstrates the enhancement of growth of environmentally stressed bacteria in the presence of BF. A stationary phase Luria Broth culture of enteropathogenic *E. coli* (EPEC) strain E2348-69 was stored continuously at 0-4° C. for 3 months. This culture was then serially diluted in sterile phosphate buffered saline and plated onto MRSAgar+/−2% BF as shown (MRSAgar only, left image; with BF, right image). Plates were incubated at 37° C. for 16 hours. The results show that BF helps to resuscitate the "viable but non culturable" population within this aged and cold damaged/nutrient starved culture.

Time Course of LAB Growth

Figure 7:
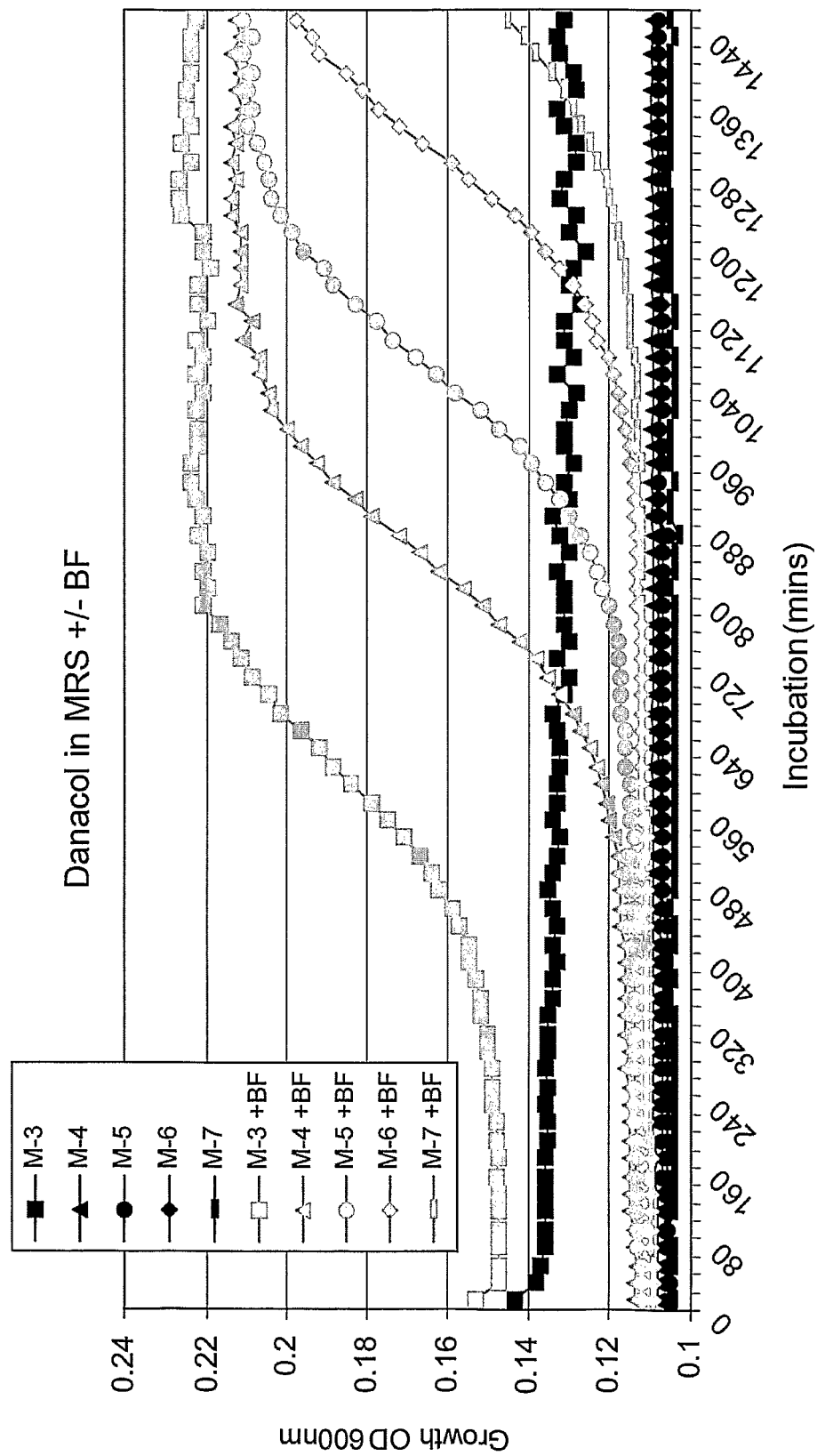
FIG. 7 shows a time course of lactic acid bacterial growth under aerobic conditions with and without banana extract

The time course of growth of LAB grown aerobically in the presence of BF is shown in FIG. 7. LAB taken directly from a commercial yoghurt drink preparation (Danacol brand, Danone manufacturer) were serially diluted into MRS medium+/−2% BF. Duplicate cultures were incubated aerobically with shaking and growth monitored continuously for 24 hours. The viable count per ml of original yoghurt was 1.06e8 CFU/ml, which means that the initial cell numbers at the beginning of each time course of growth are as follows: −3 Diln (1:1000 dilution) is equal to approximately 1.06e5 CFU/ml; −4 Diln (1:10000 dilution) approximately 1.06e4 CFU/ml; −5 Diln (1:100 000 dilution) approximately 1060 CFU/ml and the −6 Diln (1:1000 0000 dilution) is equivalent to around 100 CFU/ml. Viable counts of the end points of each of the time courses allows interpretation of the OD600 value of 0.25 to be equivalent to bacterial cell count value of around 5-6 e7 CFU/ml, indicating that in the presence of BF growth of a starting inoculum of around 100 LAB was enhanced more than 100,000-fold.

Note that there is no significant growth in the absence of BF in MRS media under these fully aerobic conditions, even after 24 hours incubation. Data for LAB from other probiotic supplements and yoghurt preparations shows similar results.

Applications of BF in LAB and Other Species Growth Enhancement Processes

Our data suggests the utility of banana extract, both pulp and peel, to enhance the growth of a variety of lactic acid bacteria strains commonly used in probiotic supplements, such as the Lactobacilli and Bifidobacteria. We have characterised the stability of banana extracts to conditions involved in typical media preparation, such as autoclaving (heating for up to 30 minutes at 121° C., 15 lbs in$^{-2}$) and freeze-drying. We have also shown that incorporation of banana extract can convert cheaper, non-specialised culture media, both liquid and solid agar based, into media on which the lactic acid bacteria can grow as comfortably as expensive bespoke LAB media. We also have data showing the utility of BF in speeding up growth of food poisoning agents such as *Listeria monocytogenes* and pathogenic *E. coli*. Thus, we have ample proof of principle data for the creation of a new and much improved media for the growth of the economically important beneficial lactic acid bacteria, which may also have applications for more rapid detection of those microbial species that can pose danger to humans.

Figure 8:
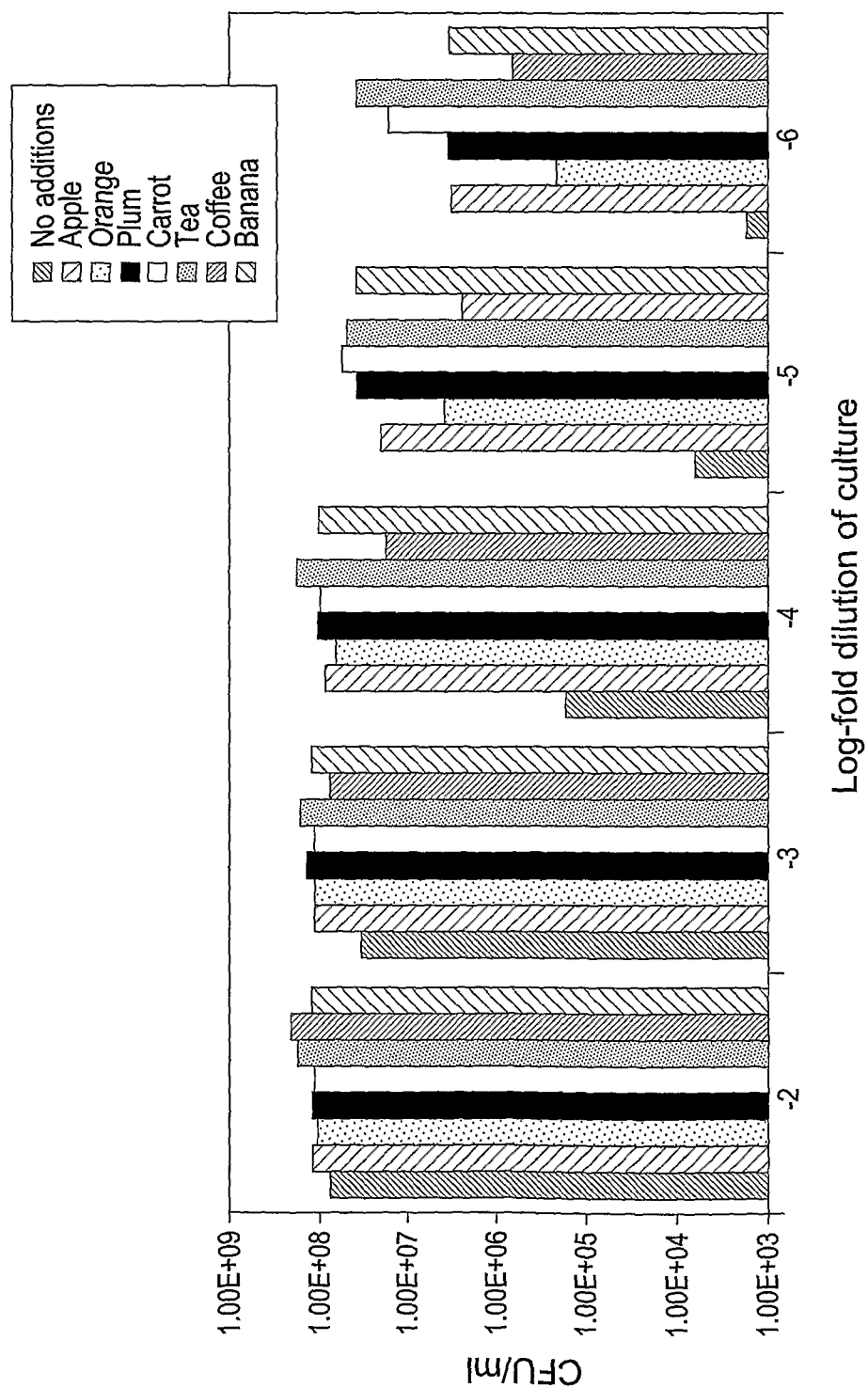
FIG. 8 shows the growth response of L. casei to various fruit, vegetable and beverage extracts compared with banana extract

Growth Promotion by Other Edible Plant-Derived Extracts of LAB and Other Microbial Species Although extracts prepared from *Musa* fruit contain highly potent growth enhancement compounds as indicated by the data shown in FIGS. 3-7, we also have discovered that extracts prepared from other fruit, vegetables and plant tissues used in beverage preparation also possess activities which may be beneficial to growth and resuscitation of LAB and other bacterial species. FIG. 8 shows the effects of juice (2% v/v) from apple, orange, plum, carrot, and infusions (2% v/v) from tea (prepared from 1 teabag infused for 60 seconds in 200 ml of boiling water) and coffee (prepared from 3 g of instant coffee dissolved in 200 ml boiling water) on the growth of *L. casei* in serum-SAPI medium; responses of the same culture dilutions to a banana (BF) extract are shown for comparison. Cultures were incubated as described in the legend to FIG. 2, and growth enumerated on MRS agar. Given that the extracts shown generally induce comparable levels of growth to banana, their potential for use in applications similar to those suggested for *Musa*-derived extracts is clear.

Yoghurt Viability and Efficacy Improvement Through Use of BF

In order to demonstrate the potential benefits of BF improving the quality and durability of probiotic yoghurts a series of tests was set up using a range of market leading probiotic yoghurts and drinks.

1. We analysed effects on leading once-a-day probiotic yoghurts to investigate whether the addition of BF could have a beneficial effect on the overall numbers of viable bacteria persisting within a refrigerated once-a-day dose of probiotic bacteria.

The experimental set up involved aseptically decanting commercially available suspensions of probiotic yoghurt bacteria, aliquotting them into triplicate sterile 25 ml plastic tubes supplemented with and with 1% (15 units/ml) of BF. The covers of these tubes were loosely closed, to maintain exposure to atmospheric oxygen without compromising microbiological sterility, and stored upright in a refrigerator set at 4° C. At the times indicated, culture samples were aseptically withdrawn and viability counts determined using culture on MRS agar; all viable counts were performed in triplicate, and showed standard errors of less than 2%. All experiments were also performed on at least 2 separate occasions, and are fully reproducible.

Figure 9:
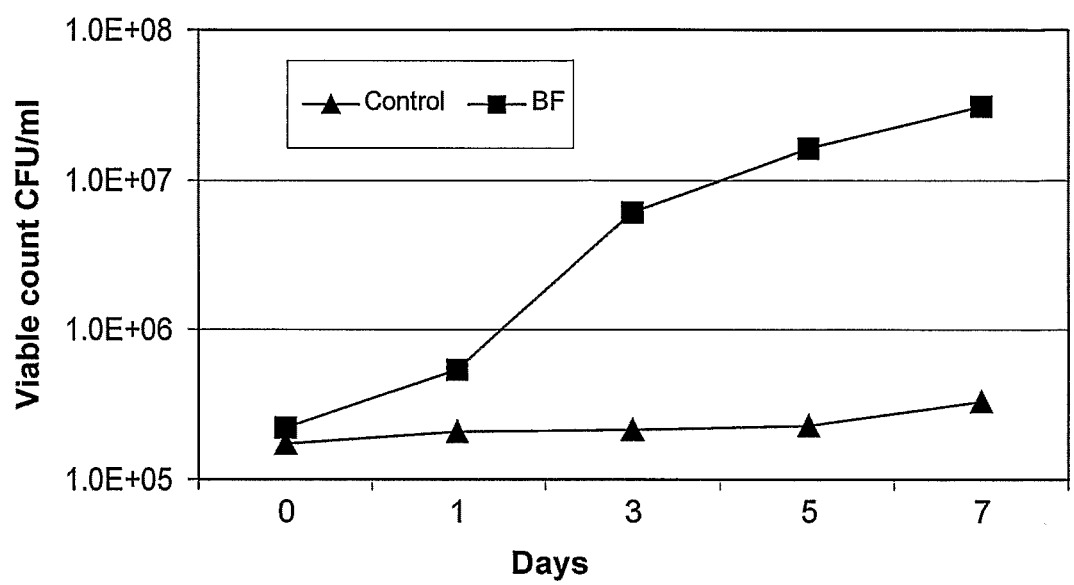
FIG. 9 shows the effect of banana extract on the viability of probiotic lactic acid bacteria

It should be noted that for the yoghurt examined, the manufacturer's website estimation of the initial viable count (colony forming units, CFU/ml) of the preparation was around $10^8$ CFU/ml. However, initial measurements at time 0, shown in FIG. 9, indicate a viable count of nearer $10^5$ CFU/ml. Over the 7 days of the time course shown in FIG. 9 there was no significant reduction in viability within the control cultures. However, data from the yoghurt samples with added BF indicates that there is a significant difference ($P<0.001$) in the level of viable cells occurring in the presence of BF. After about 3 days pre-incubation with BF there was a significant increase in the overall viability of the bacteria within the yoghurt suspension, peaking at about 7 days (the experiment was continued for a further 4 days, with no more significant changes in viable count, data not shown). In total, BF increased the level of viable lactic acid bacteria (as determined by plate culture) by over 140-fold. It is unlikely that the increase in viable cell count observed in FIG. 9 represents an increase in numbers as a consequence of cell division as lactic acid bacteria, particularly probiotic strains, are mesophilic in terms of optimal growth temperature. Also, the optical density readings of the cultures did not increase during the course of the experiment, which would be expected if a >100-fold increase in cellular biomass had occurred. The data in FIG. 9 therefore indicates that a significant proportion of the bacteria in the yoghurt preparation investigated were dormant and that BF is bringing back the culture to a level of viability present when the yoghurt was initially manufactured.

Figure 10:
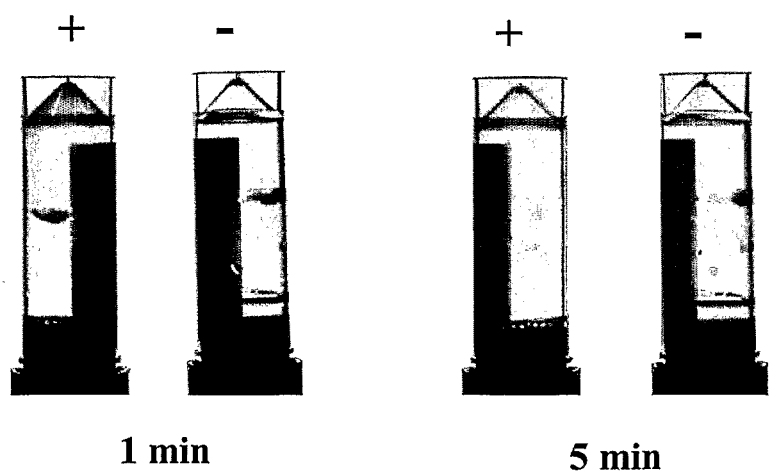
FIG. 10 shows the effect of banana extract on the adherence of lactic acid bacteria to a surface

2. Additional tests of the culture in the yoghurt preparation shown in FIG. 9 also indicates that BF appears to be augmenting the viscosity and ability of the probiotic lactic acid bacteria examined to attach to surfaces; with the effect being seen within 3 days of incubation at 4° C. (FIG. 10). The pictures show adherence of probiotic lactic acid yoghurt suspensions 1 and 5 minutes after inversion. In the presence of BF, it can clearly be seen that attachment of bacteria to the rear of the plastic tube is substantially greater compared to un-supplemented control cultures. This effect was observed in at least 20 separate experiments. BF-supplemented cultures are also more viscous, as can be seen in the greater number of bubbles in the air-liquid interfaces.

In terms of the explanation for the data in FIG. 10, it is possible that the increase in viscosity and surface attachment observed is mediated in part by increased exopolysaccharide production by the bacteria. This is a potentially important benefit additional to the improved viability observed in FIG. 9, since the contribution of lactic acid bacteria exopolysaccharide to yoghurt texture is well recognised. In addition, it is also likely that any augmentation in the ability of the lactic acid bacteria to adhere to surfaces will have a direct effect on the ability of these bacteria to attach to the gastrointestinal epithelia, and therefore be of benefit in the ability of the probiotic lactic acid bacteria to colonise the host gut.

As well as enhancing growth, it now also appears from the data in FIGS. 9 and 10 that BF is additionally capable of resurrecting environmentally stressed and damaged lactic acid bacteria which were previously non-viable, giving a boost to their metabolism which renders them fully culturable as well as possibly increasing their potential for host colonisation.

The invention claimed is:

1. A method of enhancing or promoting growth or viability of bacteria selected from the group consisting of: Gram positive bacteria, and lactic acid bacteria, the method comprising:
   preparing an extract obtained from *Musa* spp by:
      blending at least a portion of a *Musa* fruit in a suitable diluent to form a liquidized intermediary;
      centrifuging the liquidized intermediary to form a juice and a debris pellet;
      decanting the juice from the debris pellet to form the extract; and
      autoclaving the extract;
   introducing an enhanced bacterial growth medium consisting of a serum-free bacterial growth medium supplemented with the extract to said bacteria, wherein the extract is present in said medium at a concentration of between 0.01 and 10%; and
   culturing an isolated bacterial sample of said bacteria on said growth medium to thereby enhance or promote growth or viability of said bacteria over that which would be obtained with a medium typically used to grow said bacteria in the absence of said extract;
   wherein said bacterial growth medium is capable of enhancing growth of said bacteria from an OD600 value of 0.1 to at least 0.145 over an incubation period of at least 1480 minutes, or
   wherein said bacterial growth medium is capable of enhancing viability of said bacteria from $10^5$ colony forming units (CFU)/ml to at least $10^7$ CFU/ml over 7 days.

2. The method of claim 1 wherein the extract is obtained from banana skin and/or banana pulp.

3. The method of claim 1 wherein the bacteria are lactic acid bacteria.

4. The method of claim 1 wherein the bacteria are environmentally stressed prior to growth with the extract.

5. The method of claim 1, wherein the culturing of the bacteria is in a non-anaerobic environment.

6. The method of claim 1, wherein the sample is taken from a food product, or a brewing or winemaking product.

7. The method of claim 1, wherein preparing the extract comprises any or all of the following additional steps: filtering the extract; drying or lyophilizing the extract; and freezing the extract.

8. A method, comprising:
   introducing a bacterial growth medium selected from the group consisting of deMann Rogan Sharpe (MRS) and Luria, the bacterial growth medium supplemented with an extract obtained from a plant selected from the group consisting of: *Musa* spp, and a species of apple, orange, plum, carrot, tea, or coffee to bacteria, wherein the extract is present in said medium at a concentration of 0.01 to 10%; and
   culturing an isolated bacterial sample of said bacteria on said growth medium to thereby enhance adherence to a substrate, or to promote viability, or viscosity, said bacteria being selected from the group consisting of: Gram positive bacteria and lactic acid bacteria,
   wherein said bacterial growth medium is capable of enhancing viability of said bacteria from $10^5$ colony forming units (CFU)/ml to at least $10^7$ CFU/ml over 7 days.

9. The method of claim 8, wherein the extract is obtainable or obtained from *Musa* spp.

10. The method of claim 8, wherein the bacteria are lactic acid bacteria.

11. The method of claim 8, wherein the extract is present in said medium at a concentration of between about 0.1 to 5%.

12. The method of claim 11, wherein the extract is present in said medium at a concentration of between about 1 to 2%.

13. The method of claim 8, wherein the medium does not comprise serum, and wherein the supplement comprises no additional nutrient components.

14. The method of claim 8, wherein the extract does not substantially comprise catecholamines and/or fructo-oligosaccharides.

15. The method of claim 8, further comprising preparing the extract by:
   blending at least a portion of a Musa fruit in a suitable diluent to form a liquidized intermediary;
   centrifuging the liquidized intermediary to form a juice and a debris pellet;
   decanting the juice from the debris pellet to form the extract; and
   autoclaving the extract.

16. The method of claim 1, wherein the extract is present in said medium at a concentration of between about 1 to 2%.

17. The enhanced bacterial growth medium of claim 1, wherein the bacterial growth medium is selected from the group consisting of MRS and Luria.

18. The method of claim 1, wherein the extract is autoclaved at 121° C. and 103 kPa for 15 minutes.

* * * * *